United States Patent

Sato et al.

[11] Patent Number: 4,474,881
[45] Date of Patent: Oct. 2, 1984

[54] PROCESS FOR PREPARING POLYPRENYL CARBOXYLIC ACID DERIVATIVES

[75] Inventors: Akio Sato; Kenji Nakajima; Yoshimasa Takahara, all of Yatabemachi; Shizumasa Kijima, Niiza; Yuichi Inai, Tokyo; Yoshiyuki Kohara, Gifu; Yoshiyuki Kawakami, Tokyo; Tomio Tsurugi, Gifu, all of Japan

[73] Assignees: Eisai Co., Ltd.; Agency of Industrial Science and Technology, both of Tokyo, Japan

[21] Appl. No.: 392,831

[22] Filed: Jun. 28, 1982

Related U.S. Application Data

[62] Division of Ser. No. 259,772, May 1, 1981.

[30] Foreign Application Priority Data

May 19, 1980 [JP] Japan ................... 55-66203

[51] Int. Cl.³ .................... C12P 7/40; C12P 7/00; C12N 9/02; C12N 1/20
[52] U.S. Cl. ................. 435/136; 435/132; 435/189; 435/253; 435/872
[58] Field of Search ............. 435/132, 136, 189, 253, 435/872

[56] References Cited

U.S. PATENT DOCUMENTS 4,338,251 7/1982 Sato et al. ................ 435/134
4,386,227 5/1983 Sato et al. ................ 568/875

FOREIGN PATENT DOCUMENTS 6124387 9/1981 Japan ................... 435/136

*Primary Examiner*—Thomas Wiseman
*Assistant Examiner*—Deborah A. Grossman
*Attorney, Agent, or Firm*—Flynn, Thiel, Boutell & Tanis

[57] ABSTRACT

A process is disclosed for the preparation of a compound having the general formula:

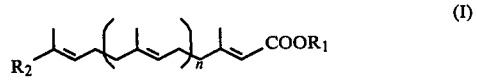

(I)

wherein n is an integer of from 2 to 4, $R_1$ is an ester-forming moiety effective as a protecting group for a carboxyl group, and $R_2$ is hydroxymethyl, formyl or carboxyl. The compounds (I) are useful as intermediates for the preparation of polyprenyl compounds having hypotensive and anti-ulcer activity. The process of the invention includes cultivating a microorganism selected from a strain of the genus Nocardia called BPM 1613, FERM-P No. 1609, Corynebacterium equi IAM 1038, Candida lipolytica IFO 0746, and Mycobacterium smegmatis IFO 3083, in a nutritive culture medium, in the presence of a compound having the general formula:

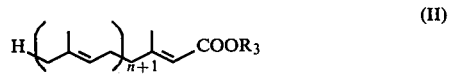

(II)

wherein $R_3$ is an ester-forming moiety effective as a protecting group for a carboxyl group, whereby the microorganism utilizes the compound (II) as a carbon source and oxidizes the compound (II), thereby converting the compound (II) into the compound (I).

8 Claims, No Drawings

PROCESS FOR PREPARING POLYPRENYL CARBOXYLIC ACID DERIVATIVES

This is a division of application Ser. No. 259,772, filed May 1, 1981.

This invention relates to new polyprenyl carboxylic acid derivatives and a process for the preparation of the same. The polyprenyl carboxylic acid derivatives according to the present invention have the general formula (I):

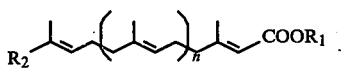
(I)

in which n is an integer of from 2 to 4, $R_1$ represents hydrogen or a protecting group for the carboxyl group, and $R_2$ represents a hydroxymethyl, formyl or carboxyl group.

In the above-mentioned general formula (I), the protecting group for the carboxyl group is generally an ester residue. More concretely, examples of the protecting groups include an alkyl ($C_{1-4}$) group such as methyl, ethyl, propyl or butyl; an alkenyl group such as allyl, geranyl or farnesyl; a cycloalkyl group such as cyclohexyl; and an aryl group such as phenyl or tolyl.

The compound of the present invention is of value as an intermediate compound for preparing polyprenyl carboxylic acids having the general formula (A):

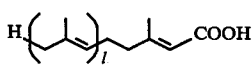
(A)

in which l is an integer of from 4 to 11, and its esters that are heretofore known compounds. The hypotensive activity and the anti-ulcer activity of these compounds are disclosed in Japanese Patent Provisional Publications No. 52(1977)-144614 and No. 54(1979)-5043, respectively.

The compound of the general formula (A) can be, for instance, prepared from the compound of the present invention by a process which is conducted via a sulfone derivative as disclosed in Japanese Patent Provisional Publications No. 53(1978)-103444 and No. 53(1978)-103445. The compound of the general formula (I) in which $R_2$ represents the hydroxymethyl group can be used as an intermediate compound. Otherwise, the compound of the general formula (I) in which $R_2$ represents a formyl or carboxyl group can be reduced to the compound (I) in which $R_2$ represents the hydroxymethyl group.

The reactions can be, for instance, illustrated as follows:

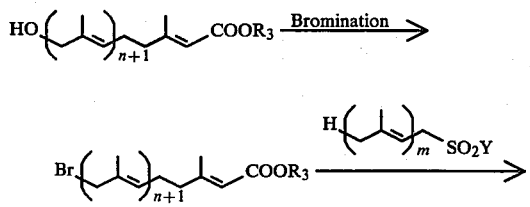

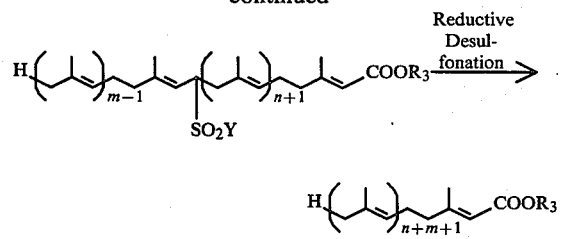

In the above-illustrated formulae, n is an integer of from 2 to 4, m is an integer, $R_3$ represents a protecting group for the carboxyl group, and Y represents an aryl or alkyl group.

The compound of the general formula (A) and its ester can be also prepared through the Wittig reaction of a polyprenyl aldehyde with the bromo-compound shown in the above-illustrated reaction equation.

As shown in the above, the employment of the compound of the invention in the preparation of polyprenyl carboxylic acid and its ester can increase the carbon number of the carbon chain by 20 to 30 at a time.

Further, various kinds of polyprenyl alcohols can be prepared from a dihydroxy compound which is obtained by reducing the compound of the invention, in the same manner as the above-described carbon chain lengthening reaction. The polyprenyl alcohols have been known to be intermediate compounds useful for the preparation of pharmacologically active compounds, and are further known as having hypotensive activity, as disclosed in Japanese Patent Provisional Publications No. 54(1979)-70430 and No. 54(1979)-76513.

As described hereinabove, the compound of the present invention is of value as an intermediate compound for the preparation of pharmacologically active compounds, and also has anti-ulcer activity and hypotensive activity.

The compound the present invention can be obtained by oxidizing microbiologically a polyprenyl carboxylic acid with a microorganism belonging to the genus Nocardia.

The microbiological characteristics of the strain belonging to the genus Nocardia named BPM 1613 that has been deposited with the Fermentation Research Institute, the Agency of Industrial Science and Technology at 1-1-3, Higashi, Tsukuba-Yatabe-machi, Ibaraki-prefecture, Japan, has been added to its permanent collection of microorganisms as FERM-P No. 1609, and which can be employed for the present invention, are given below. The same Nocardia, BPM 1613 has been deposited also with the Institute for Fermentation, Osaka, 17-85 Juso-honmachi 2-chome, Yodogawa-ku, Osaka, Japan, as deposition number IFO 14101. The color is expressed according to the "Color Standard" published by Nippon Shikisai Kenkyusho (Japan Color Research Center), Japan.

A. Form of Cells

The present strain shows characteristic orange to pink color in almost all culture media, as seen from the cultural characteristics given below. A young vegetative cell grows in a mycelial form, and branching is rarely observed. In an aged cultivated system, the hypha is divided to form a bacillus (0.4–0.6 × 1.8–2.4μ). Gram positive. No flagellum. Negative on the acid-fast stain according to the Ziehl-Nielsen method. Aerial mycelium is not observed.

B. Cultural Characteristics on Various Media
(1) Sucrose—Nitrate Agar Medium (30° C.) poor growth; pink colored colony; no diffusive pigment
(2) Glucose—Asparagine Agar Medium (30° C.) no growth
(3) Glycerol—Asparagine Agar Medium (30° C.) poor growth; pink colored colony; no diffusive pigment
(4) Starch Agar Medium (30° C.) no growth
(5) Tyrosine Agar Medium (30° C.) poor growth; grayish white colored colony; no diffusive pigment
(6) Nutrient Agar Medium (30° C.) moderate growth; orange colored colony; no diffusive pigment
(7) Yeast—Malt Agar Medium (30° C.) rich growth; orange colored colony; no diffusive pigment
(8) Oatmeal Agar Medium (30° C.) moderate growth; orange colored colony; no diffusive pigment
(9) Calcium Maleate Agar Medium (27° C.) moderate growth; pink colored colony
(10) Ovalbumin Medium (slant, 27° C.) poor growth; white colony
(11) Potato Section Medium (27° C.) moderate growth; pale orange colored colony
(12) Carrot Section Medium (27° C.) moderate growth; pale pink colored colony C. Physiological characteristics
(1) Growth Temperature Range (on Nutrient Agar Medium, slant): 20°–42° C.
(2) Liquefaction of Gelatin: negative
(3) Hydrolysis of Starch: negative
(4) Coagulation of Defatted Milk, Peptonization: negative
(5) Litmus Milk: no change
(6) Production of Melanine-like Pigment: negative
(7) Reduction of Nitrate: positive
(8) No gas or acid production from L-arabinose, D-xylose, D-glucose, D-fructose, sucrose, D-mannitol, glycerol, lactose, D-galactose, D-mannose, maltose, trehalose, starch
(9) Catalase Test: negative
(10) Production of Indole: negative
(11) Production of Hydrogen Sulfide: negative D. Assimilability for Various Carbon Sources
(Pridham-Gottlieb Agar Medium, 30° C., 7 days)
L-arabinose (+), D-xylose (+), D-glucose (++), D-fructose (++), sucrose (++), inositol (+), L-rhamnose (−), raffinose (+), D-mannitol (+) (In the above, (++) means moderate growth, (+) means poor growth, and (−) means no growth)

The above-identified strain was cultivated on the Glycerol-Kelner-Morton Medium in accordance with the method described by Arai et al. in Journal of General Applied Microbiology, 9, 119 (1963). The Actinomycetales, The Jena International Symposium on Taxonomy, 273 (1968) gives absorption bands characteristic of the genus Nocardia on the IR spectrum, that is, I: C & E types, II: C type, III: C type, IV: D type.

Upon studying the above-described characteristics of the strain with reference to Bergey's Manual of Determinative Bacteriology, seventh edition, and Waksman's The Actinomycetes, Volume 2, the strain was determined to belong to the genus Nocardia.

A process for the preparation of the compound of the present invention is described hereinbelow.

The polyprenyl carboxylic acid derivatives (I) of the present invention can be prepared by a process comprising:

cultivating a microorganism belonging to the genus Nocardia and showing oxidizing activity on a compound having the general formula (II):

in which n has the same meaning as defined hereinbefore, and $R_3$ represents a protecting group for the carboxylic acid group in a culture medium containing a compound of the general formula (II) as the carbon source;

recovering the so-oxidized product; and hydrolyzing the so recovered product, if necessary, to give the product having the general formula (I):

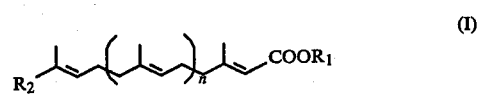

in which n, $R_1$ and $R_2$ have the same meanings as defined hereinbefore.

Examples of the protecting groups $R_3$ for the carboxyl group of the general formula (II) are the same as those of the protecting groups $R_1$ for the carboxyl group in the aforesaid general formula (I).

Any microorganism showing an oxidizing activity on the compound of the general formula (II) can be employed in this process. For example, the strain genus Nocardia named BPM 1613 mentioned hereinbefore, *Corynebacterium equi* IAM 1038, *Candida lipolytica* IFO 0746, and *Mycobacterium smegmatis* IFO 3083 can be employed.

The cultivation procedure is now described more concretely hereinbelow.

The components of the culture medium can be optionally chosen from those conventionally employed, except for the inclusion of the compound of the general formula (II) as the carbon source. Examples of nitrogen sources include nitrates such as potassium nitrate, sodium nitrate and ammonium nitrate, and ammonium salts such as ammonium chloride, ammonium sulfate and ammonium phosphate, and ammonia and urea. If necessary, inorganic salts such as potassium phosphate, sodium phosphate, magnesium sulfate, ferrous sulfate and manganese sulfate, and organic nutrient sources such as vitamins and amino acids, yeast extract, corn steep liquor, and malt extract containing the vitamins and amino acids, can be incorporated.

The medium is preferably adjusted to be alkaline in the pH range of 7–10. The cultivation is generally carried out under aerobic conditions such as under aeration and agitation at 20°–40° C. for 2–4 days.

After the cultivation is complete, the cultivation product is extracted with an organic solvent such as ethyl ether, benzene or chloroform to recover the compound of the invention. The product can be separated and purified through silica gel column chromatography. The unreacted starting compound can be recovered in the course of the above-mentioned extraction procedure and column chromatography, and can be employed again as the starting compound for the process of the invention.

The carboxyl-protecting group of the resulting compound can be eliminated from the so-obtained product through a conventional method for hydrolysis of carboxylic acid esters. For example, the elimination can be carried out in the presence of a base such as sodium hydroxide or potassium hydroxide.

The microbiological oxidation of the present process gives different products having hydroxymethyl, formyl and carboxyl groups, respectively, at the terminal $R_2$ group, depending upon the extent of the oxidation. The constitution of the product, accordingly, can be varied depending upon the cultivation conditions and the kinds of protecting groups used for the carboxyl group of the starting compound.

The present invention is further described more in greater detail in the following examples.

EXAMPLE 1

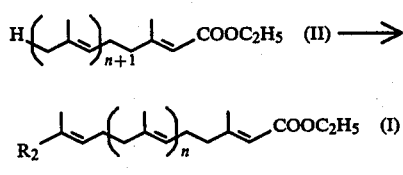

The strain (BPM 1613, FERM-P No. 1609) belonging to the genus Nocardia was precultivated under shaking at 30° C. for 4 days in 50 ml of a medium comprising 2% of n-paraffin, 0.5% of $NaNO_3$, 0.15% of $KH_2PO_4$, 0.15% of $Na_2HPO_4$, 0.05% of $MgSO_4.7H_2O$, 0.001% of $FeSO_4.7H_2O$, 0.001% of $CaCl_2.2H_2O$, and 0.02% of yeast extract and having the pH value of 7.2.

Then, the so obtained precultural broth was inoculated, in the volume ratio of 8% into a jar fermentor (for fermentation of 1 liter medium) with a medium having the same composition as defined above except substituting the n-paraffin (2%) with the compound of the general formula (II) (1%). The cultivation was carried out under aeration-agitation conditions at 30° C. for 3 days. After cultivation was complete, the cultivation product was extracted with ethyl ether. The solvent was distilled off, and the residue was purified by the silica gel column chromatography. In the chromatography, hexane and ethyl ether were employed as the developing solvents.

The products obtained in the above process are set forth in Table 1.

TABLE 1

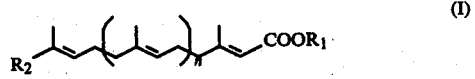

| n | $R_2$ | State Yield (%) | Mass Spectrum (M+) | NMR (δ, CDCl₃) |
|---|---|---|---|---|
| 2 | HOOC— | oil 21 | 362 | 1.25 (3H, t), 1.58 (6H, s), 1.81 (3H, s), 1.94~2.40 (15H), 4.10 (2H, q), 5.05 (2H, br), 5.60 (1H, s), 6.84 (1H, t), 11.20 (1H, br) |
|   | OHC— | oil 1.5 | 346 | 1.25 (3H, t), 1.58 (6H, s), 1.75 (3H, s), 1.93~2.40 (15H), 4.10 (2H, q), 5.05 (2H, br), 5.60 (1H, s), 6.40 (1H, t), 9.39 (1H, s) |
|   | HOH₂C— | oil 12 | 348 | 1.25 (3H, t), 1.58 (6H, s), 1.64 (3H, s), 1.90~2.40 (16H), 3.95 (2H, s), 4.10 (2H, q), 5.04 (2H, br), 5.22 (1H, t), |

TABLE 1-continued

| n | $R_2$ | State Yield (%) | Mass Spectrum (M+) | NMR (δ, CDCl₃) |
|---|---|---|---|---|
| 3 | HOOC— | oil 32 | 430 | 5.60 (1H, s) 1.25 (3H, t), 1.59 (9H, s), 1.82 (3H, s), 1.90~2.42 (19H), 4.10 (2H, q), 5.06 (3H, br), 5.64 (1H, s), 6.89 (1H, t), 11.10 (1H, br) |
|   | OHC— | oil 2.0 | 414 | 1.25 (3H, t), 1.59 (9H, s), 1.75 (3H, s), 1.86~2.40 (19H), 4.10 (2H, q), 5.06 (3H, br), 5.62 (1H, s), 6.43 (1H, t), 9.37 (1H, s) |
|   | HOH₂C— | oil 14 | 416 | 1.25 (3H, t), 1.58 (9H, s), 1.64 (3H, s), 1.80~2.35 (20H), 3.95 (2H, s), 4.10 (2H, q), 5.06 (3H, br), 5.35 (1H, br), 5.62 (1H, s) |
| 4 | HOOC— | oil 26 | 498 | 1.25 (3H, t), 1.59 (12H, s), 1.81 (3H, s), 1.85~2.40 (23H), 4.11 (2H, q), 5.05 (4H, br), 5.61 (1H, s), 6.87 (1H, t), 11.00 (1H, br) |
|   | OHC— | oil 2.2 | 482 | 1.25 (3H, t), 1.59 (12H, s), 1.74 (3H, s), 1.85~2.40 (23H), 4.11 (2H, q), 5.05 (4H, br), 5.63 (1H, s), 6.45 (1H, t), 9.39 (1H, s) |
|   | HOH₂C— | oil 18 | 484 | 1.25 (3H, t), 1.59 (12H, s), 1.65 (3H, s), 1.85~2.42 (24H), 3.96 (2H, s), 4.11 (2H, q), 5.05 (4H, br), 5.35 (1H, br), 5.63 (1H, s) |

We claim:

1. A process for the preparation of a polyprenyl carboxylic acid derivative having the general formula:

$$R_2 \diagdown \cdots \diagdown COOR_1 \quad (I)$$

wherein n is an integer of from 2 to 4, $R_1$ is an ester-forming moiety effective as a protecting group for a carboxyl group, and $R_2$ is hydroxymethyl, formyl or carboxyl, which comprises the steps of:

cultivating a microorganism selected from the group consisting of a strain of the genus Nocardia called BPM 1613, FERM-P No. 1609, *Corynebacterium equi* IAM 1038, *Candida lipolytica* IFO 0746, and *Mycobacterium smegmatis* IFO 3083, in a nutritive culture medium, in the presence of a compound having the general formula:

$$H \diagdown \cdots \diagdown COOR_3 \quad (II)$$

wherein $R_3$ is an ester-forming moiety effective as a protecting group for a carboxyl group, whereby said microorganism utilizes said compound (II) as a carbon source and oxidizes said compound (II), thereby converting said compound (II) into said compound (I); and isolating said compound (I).

2. A process as claimed in claim 1, further comprising the steps of precultivating said microorganism in said nutritive culture medium, before said cultivation step, using a carbon source other than said compound (II); extracting a mixture formed by said cultivation step with an organic solvent to obtain a cultivation product therefrom; removing said organic solvent from said cultivation product; and subjecting said cultivation product to column chromatography to isolate said compound (I).

3. A process for the preparation of a compound of the general formula:

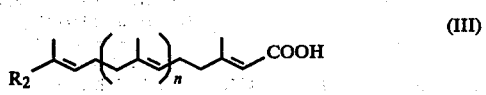 (III)

comprising hydrolyzing a compound of the formula (I) prepared by the process as claimed in claim 1 to remove the protecting group $R_1$ therefrom; and isolating said compound (III).

4. A process as claimed in claim 1, wherein said protecting groups $R_1$ and $R_3$ are each selected from the group consisting of $C_1-C_4$ alkyl, alkenyl, cycloalkyl and aryl.

5. A process as claimed in claim 1, wherein said protecting groups $R_1$ and $R_3$ are each selected from the group consisting of methyl, ethyl, propyl, butyl, allyl, geranyl, farnesyl, cyclohexyl, phenyl and tolyl.

6. A process as claimed in claim 1, wherein said culture medium has a pH in the range of 7 to 10, and said cultivation step is carried out under aerobic conditions with agitation at 20° to 40° C. for 2 to 4 days.

7. A process as claimed in claim 1, wherein said culture medium comprises a nitrogen source selected from the group consisting of potassium nitrate, sodium nitrate, ammonium nitrate, ammonium chloride, ammonium sulfate, ammonium phosphate, ammonia and urea, an inorganic salt selected from the group consisting of potassium phosphate, sodium phosphate, magnesium sulfate, ferrous sulfate and magnesium sulfate, and an organic nutrient source selected from the group consisting of vitamins, amino acids, yeast extract, corn steep liquor and malt extract.

8. A process for the preparation of a polyprenyl carboxylic acid derivative having the general formula:

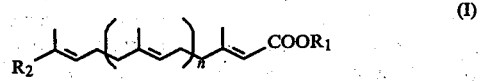 (I)

wherein n is an integer of from 2 to 4, $R_1$ is an ester-forming moiety effective as a protecting group for a carboxyl group, and $R_2$ is hydroxymethyl, formyl or carboxyl, which comprises the steps of:
cultivating a microorganism belonging to the genus Nocardia called BPM 1613, FERM-P No. 1609 in a nutritive culture medium, in the presence of a compound having the general formula:

 (II)

wherein $R_3$ is an ester-forming moiety effective as a protecting group for a carboxyl group, whereby said microorganism utilizes said compound (II) as a carbon source and oxidizes said compound (II), thereby converting said compound (II) into said compound (I); and
isolating said compound (I).

* * * * *

UNITED STATES PATENT AND TRADEMARK OFFICE
CERTIFICATE OF CORRECTION

PATENT NO. : 4 474 881
DATED : October 2, 1984
INVENTOR(S) : Akio SATO et al

It is certified that error appears in the above-identified patent and that said Letters Patent is hereby corrected as shown below:

Column 7, line 12; change the formula to read as follows:

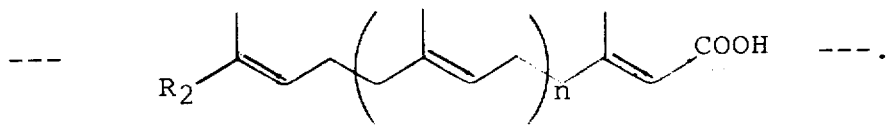

Signed and Sealed this

Twelfth Day of March 1985

[SEAL]

Attest:

DONALD J. QUIGG

Attesting Officer    Acting Commissioner of Patents and Trademarks